United States Patent
Poirier et al.

(10) Patent No.: US 8,365,723 B2
(45) Date of Patent: Feb. 5, 2013

(54) FILTER CARTRIDGE HAVING CONE OF VISIBILITY FOR END-OF-SERVICE-LIFE-INDICATOR (ESLI)

(75) Inventors: Richard J. Poirier, White Bear Lake, MN (US); Thomas W. Holmquist-Brown, St. Paul, MN (US); Neal A. Rakow, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 863 days.

(21) Appl. No.: 12/470,920

(22) Filed: May 22, 2009

(65) Prior Publication Data

US 2010/0294274 A1    Nov. 25, 2010

(51) Int. Cl.
*A62B 9/00* (2006.01)

(52) U.S. Cl. ......... 128/202.22; 128/205.29; 128/206.16; 128/206.17

(58) Field of Classification Search ............. 128/202.22, 128/202.24, 205.27–205.29, 206.16–206.17
See application file for complete search history.

(56) References Cited

U.S. PATENT DOCUMENTS

| | | |
|---|---|---|
| 1,537,519 A | 5/1925 | Yablick |
| 3,841,484 A | 10/1974 | Domnick |
| 3,966,440 A | 6/1976 | Roberts |
| 4,146,887 A | 3/1979 | Magnante |
| 4,154,586 A | 5/1979 | Jones et al. |
| 4,326,514 A | 4/1982 | Eian |
| 4,365,627 A | 12/1982 | Wing |
| 4,468,236 A | 8/1984 | Bauer |
| 4,530,706 A | 7/1985 | Jones |
| 4,684,380 A | 8/1987 | Leichnitz |
| 4,847,594 A | 7/1989 | Stetter |
| 4,873,970 A | 10/1989 | Freidank et al. |
| 5,297,544 A | 3/1994 | May et al. |
| 5,323,774 A | 6/1994 | Fehlauer |
| 5,512,882 A | 4/1996 | Stetter et al. |
| 5,666,949 A | 9/1997 | Debe et al. |
| 5,699,188 A | 12/1997 | Gilbert et al. |
| 5,882,774 A | 3/1999 | Jonza et al. |
| 5,944,873 A | 8/1999 | Jager et al. |
| 6,010,751 A | 1/2000 | Shaw et al. |
| 6,040,777 A | 3/2000 | Ammann et al. |
| 6,049,419 A | 4/2000 | Wheatley et al. |
| 6,277,178 B1 | 8/2001 | Holmquist-Brown et al. |

(Continued)

FOREIGN PATENT DOCUMENTS

| | | |
|---|---|---|
| JP | 2002-102367 | 4/2002 |
| WO | WO 95/12432 | 5/1995 |

(Continued)

OTHER PUBLICATIONS

PCT/US2010/035068 International Search Report dated Feb. 1, 2011.

(Continued)

*Primary Examiner* — Lynne Anderson

(57) ABSTRACT

A filter cartridge 12 that includes a filter material 42, an end-of-service-life-indicator 40, a cartridge housing 22, and a window 38. The filter material 42 and ESLI 40 are disposed in the housing, and the ESLI 40 may be viewed through the window 38. The window 38 is configured such that the ESLI 40 can only be seen within a cone defined by an angle θ of 20 to 70 degrees. The limited viewing range precludes reader error when examining the ESLI for color change.

20 Claims, 3 Drawing Sheets

U.S. PATENT DOCUMENTS

| | | | |
|---|---|---|---|
| 6,375,725 B1 | 4/2002 | Bernard et al. | |
| 6,497,756 B1 | 12/2002 | Curado et al. | |
| 7,201,036 B2 | 4/2007 | Custer et al. | |
| 7,320,722 B2 | 1/2008 | Mittelstadt et al. | |
| 7,419,526 B2 | 9/2008 | Greer et al. | |
| 7,442,237 B1 | 10/2008 | Gardner | |
| 2002/0026942 A1 | 3/2002 | Eswarappa | |
| 2004/0184948 A1 | 9/2004 | Rakow et al. | |
| 2004/0189982 A1 | 9/2004 | Galarneau et al. | |
| 2004/0204915 A1 | 10/2004 | Steinthal et al. | |
| 2004/0223876 A1 | 11/2004 | Kirollos et al. | |
| 2005/0161045 A1 | 7/2005 | Viner et al. | |
| 2007/0137491 A1 | 6/2007 | Attar | |
| 2007/0140907 A1 | 6/2007 | Rakow et al. | |
| 2007/0141580 A1 | 6/2007 | David et al. | |
| 2008/0063575 A1 | 3/2008 | Rakow et al. | |
| 2008/0063874 A1 | 3/2008 | Rakow et al. | |
| 2009/0133694 A1* | 5/2009 | Solci et al. | 128/202.22 |

FOREIGN PATENT DOCUMENTS

| | | |
|---|---|---|
| WO | WO 97/01778 | 1/1997 |
| WO | WO 02/22237 A1 | 3/2002 |
| WO | WO 2005/012397 A2 | 2/2005 |
| WO | WO 2009/029426 A1 | 3/2009 |

OTHER PUBLICATIONS

Budd et al., *Polymers of Intrinsic Microporosity (PIMS): Robust, Solution-Processable, Organic Microporous Materials*, Chem. Commun., 2004, pp. 230-231.

Budd et al., *Free Volume and Intrinsic Microporosity in Polymers*, J. Mater. Chem., 2005, 15, pp. 1977-1986.

McKeown et al., Chem. Eur. J., 2005, 11, No. 9, 2610-2620.

* cited by examiner

FILTER CARTRIDGE HAVING CONE OF VISIBILITY FOR END-OF-SERVICE-LIFE-INDICATOR (ESLI)

The present invention pertains to a filter cartridge that has a window through which an ESLI may be viewed. The window provides a cone of visibility so that the viewer cannot see the ESLI from an angle that could provide an erroneous reading.

BACKGROUND

Filter cartridges are commonly attached to respirator mask bodies to filter air before it is inhaled by the respirator wearer. Examples of respirator filter cartridges are shown in the following U.S. Pat. No. 7,320,722B2 to Mittelstadt et al., U.S. Pat. No. 7,419,526 to Greer et al., and U.S. Pat. No. 6,277,178 to Holmquist-Brown et al.

Some filter cartridges have an end-of-service-life-indicator, or ESLI, that provides a visible color-change signal to the respirator wearer. This visible signal (sometimes referred to as the "response signal") indicates when the filter cartridge has met the end of its useful life. Examples of cartridges that use ESLIs are described in the following U.S. Pat. Nos. 6,497,756, 4,530,706, 4,326,514, and 4,154,586. In each of these products, the filter cartridges are provided with a transparent sidewall or a shell through which the ESLI may be viewed. ESLI colorimetric sensors often exhibit a different color, depending on the angle from which the sensor is viewed. When a person does not view the ESLI normal to its positioning on the filter cartridge, there is an opportunity for the viewer to misread the indicator. A misread indicator could cause the wearer of the respirator to replace the filter cartridge too early or too late. Known filter cartridges have allowed the viewer to see the ESLI from angles of about 180° and accordingly have not addressed the issue of potential misread indicators.

SUMMARY OF THE INVENTION

The present invention provides a new filter cartridge that comprises: (a) a filter material; (b) an end-of-service-life-indicator (ESLI); (c) a cartridge housing into which the filter material and ESLI are disposed; (d) a window through which the ESLI may be viewed, the window being configured such that the ESLI can only be seen through the window within a cone defined by an angle $\theta$ of 20 to 60 degrees.

As indicated above, known filter cartridges have used sensors that are visible through the cartridge housing sidewall. These known filter cartridges have not, however, also provided a window that is configured to enable viewing only from a selected range of angles. Present invention recognizes the problem presented by known filter cartridges that contain ESLIs and provides a solution. The solution involves providing a window that is configured such that the ESLI may only be viewed through a code of visibility that is defined by an angle omega of 20 to 60°. Outside this range of visibility the viewer cannot see the ESLI and therefore cannot see a color other than the color desired to be seen when the sensor is viewed perpendicular to its planar configuration.

GLOSSARY

In this document:

"clean air" means a volume of atmospheric ambient air that has been filtered to remove contaminants;

"contaminants" means gases, vapors, and particles (including dusts, mists, and fumes) and/or other substances that generally may not be considered to be gases, vapors, or particles but which may be present in air and harmful to a person;

"end-of-service-life-indicator" or "ESLI" means a device that is capable of providing a person with information pertaining to when a filter may no longer be suitable for use due to partial or full exhaustion of the filtering capacity;

"extension" means the condition of significantly increasing size beyond a typical configuration;

"exterior gas space" means the ambient atmospheric gas space into which exhaled gas enters after passing through and beyond the mask body and/or exhalation valve;

"filter cartridge" means a structure that is primarily designed to house a filter material or filter media and that is adapted for connection to a mask body of a personal respiratory protection device;

"filter material" or "filter media" means a structure or combination of parts or elements adapted to provide clear air;

"housing" means a structure or combination of parts that is fashioned for containing another item;

"integral" means that the parts in question are made together at the same time and are not two separate parts subsequently brought together;

"interior gas space" means the space between a mask body and a person's face;

"juxtaposed" or "juxtapositioned" means placed in a general side-by-side relationship but not necessarily in contact with each other;

"mask" (when not referring to a "mask body" means having the ability to restrict the view of an object on the opposing side of the mask;

"opaque" means restricting the passage of visible light significantly more than something that is transparent;

"pane" means a planar transparent area of a window which may or may not be permeable to air;

"registration position" means the desired position of the window to provide the appropriate response signal;

"response signal" means the viewable indication that tells the viewer that the time to replace the filter cartridge has arrived;

"sorbent" means a material that is capable of capturing, occluding, or altering a contaminant through absorption, adsorption, chemisorption, decomposition, reaction, catalysis, or other suitable means;

"transparent" means that visible light can pass therethrough sufficiently to see the desired image on the opposing side of the structure modified by the word "transparent"; and "window" means a structure that provides the ability for a person to see through.

DETAILED DESCRIPTION OF PREFERRED EMBODIMENTS

Figure 1:
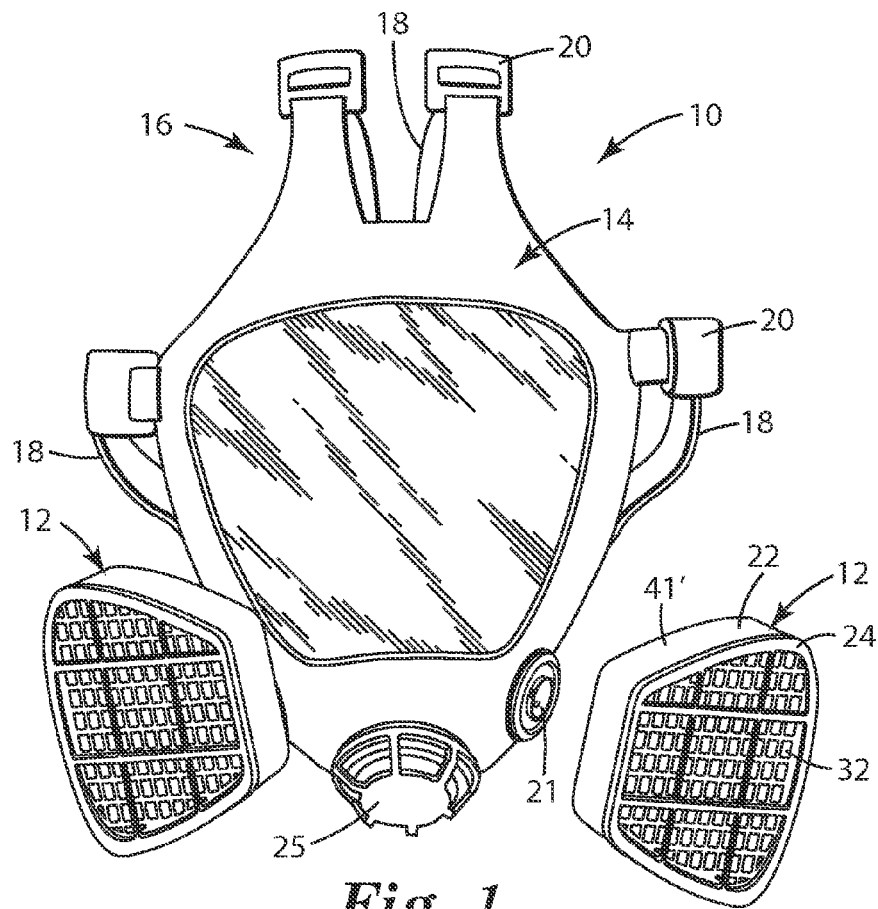
FIG. 1 is a perspective view of a respirator 10 in accordance with the present invention.

FIG. 1 shows a respirator 10 that has filter cartridges 12 that can be secured to opposing sides of the mask body 14. The mask body 14 is fashioned to snugly fit on a wearer's face. To this end, the respirator 10 includes a harness 16 for drawing the mask body 14 towards the wearer's face. The harness 16 may include one or more straps 18 for this purpose. The straps 18 may be joined to the mask body 14 and may be adjusted in length through use of buckles 20. The filter cartridges 12 may be attached to the mask body 14 by bayonet attachments 21, threading means, or any other suitable means for securing the cartridge 12 to the mask body 14. The filter cartridges 12 have a housing 22 and a cover 24, which contain a filter media for filtering ambient air that is drawn into the mask interior through the filter cartridge 12. Air that is exhaled by the user passes from the interior gas space to the exterior gas space through the exhalation valve 25.

Figure 2:
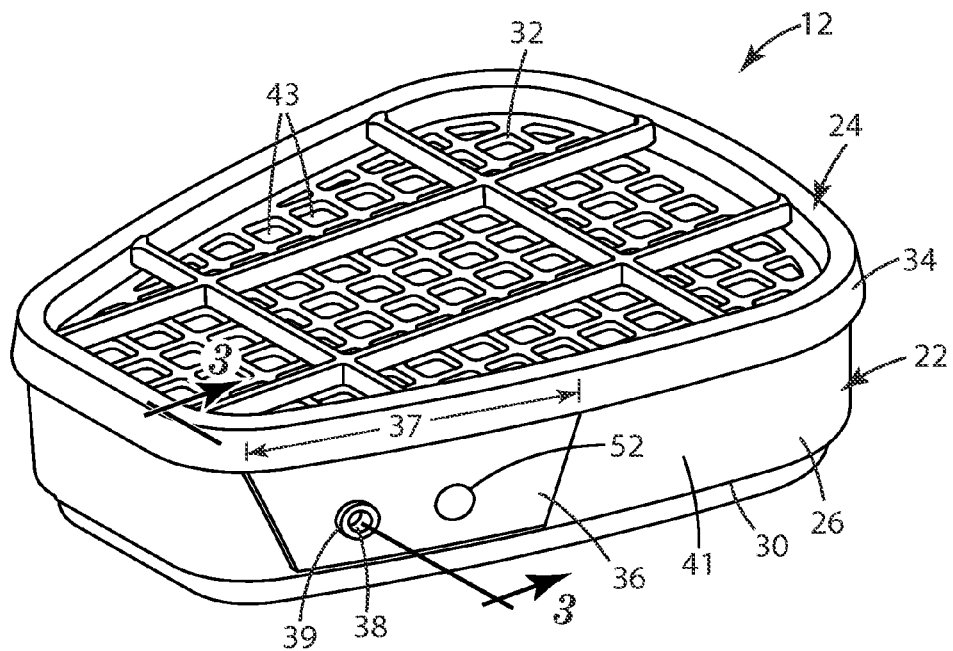
FIG. 2 is a perspective view of a filter cartridge 12 in accordance with the present invention.
Figure 3:
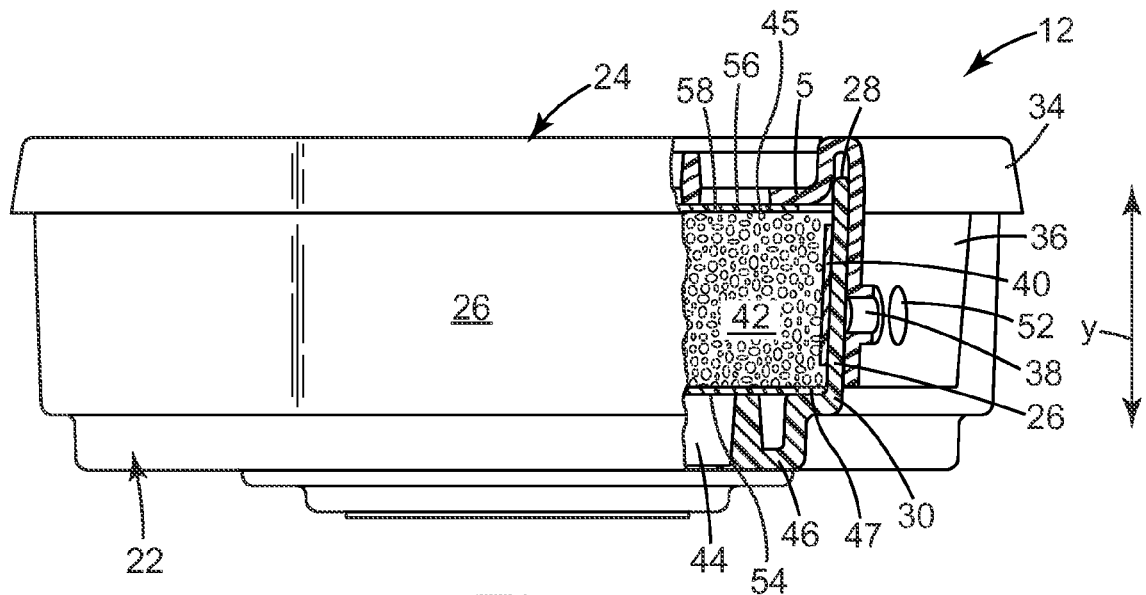
FIG. 3 is a cross-section of the filter cartridge 12 shown in FIG. 2 taken along lines 3-3.
Figure 4:
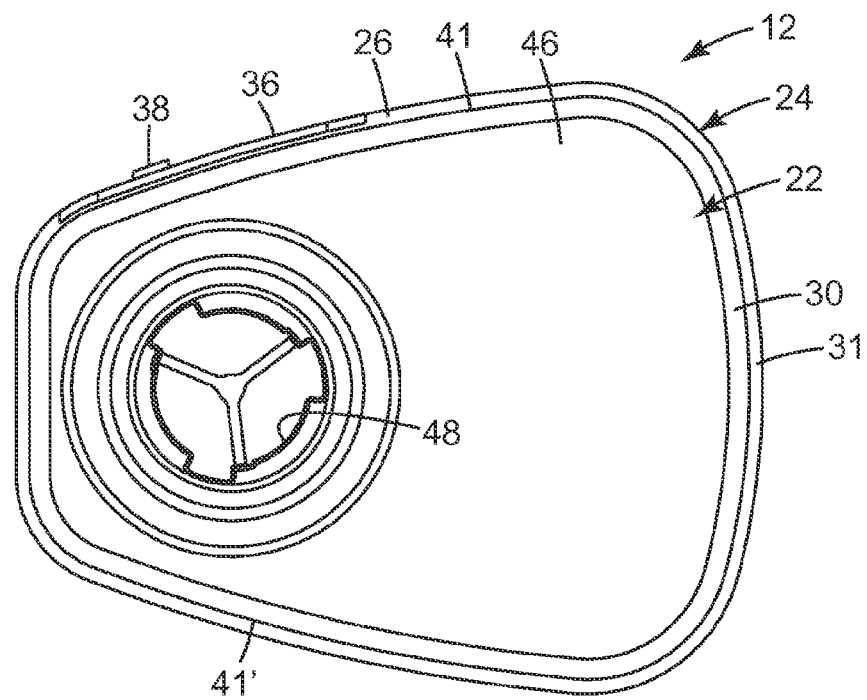
FIG. 4 is a rear view of the filter cartridge 12 shown in FIGS. 1-3.

FIGS. 2-4 illustrate that the filter cartridges 12 may include a housing 22 that has a sidewall 26 that extends from a first perimeter 28 to a second perimeter 30. The cover 24 may include an air throughput surface 32 and a securement flange 34 located along a periphery of the cover 24. The cover 24 may be secured to the sidewall 26 at the housing perimeter 28. The cover 24 may further include an opaque extension 36 that includes a window 38 located therein. The window 38 allows an end-of-service-life-indicator (ESLI) 40 to be seen therethrough. The window 38 may have an opaque frame 39 located thereabout to draw attention to the window and to encourage ESLI viewing 90 degrees to the indicator. The extension 36 may be made opaque through selection of materials that comprise the cover, for example, plastic resin or dye choice or through printing an opaque medium on the inner or outer surface of the extension 36. The whole extension 36 does not need to be opaque in order for the extension 36 to be deemed opaque. Only, for example, a portion sufficient to define the window needs to be opaque. Thus, at least some part of the extension 36 is opaque; other portions may be transparent. The extension 36 may extend away from the securement flange 34 of the cover 24 such that it resides over a substantial portion of the depth of the whole housing sidewall 26. Alternatively, the extension 36 may extend from the securement flange 34 on only one or two segments 37 of the flange 34. Thus, first and second extensions may be provided over opposing portions 41, 41' (FIG. 4) of the housing sidewall 26. The extension 36 may be configured to be about 3 to 6 centimeters (cm) long by about 1 to 2 cm wide (depth). In providing a window pane in the housing sidewall 26, the sidewall may be transparent throughout much of its whole surface or only in the vicinity of the ESLI 40 so that a person looking through the window 38 does not have an obstructed view of the ESLI 40. The ESLI may be juxtapositioned against an inner surface of the housing sidewall 26. The window 38 thus may have a first pane located in the opaque extension 36 and a second pane located in the housing sidewall 26. The first window pane may be an open pane that permits air transfer, whereas the second pane may be a solid pane impermeable to gas transfer. Additionally, a plurality of windows 38 may be used in one or more extensions to allow a plurality of ESLIs to also be used, whereby each ESLI addresses a different contaminant such as acid gases, ammonia, formaldehyde, and organic vapors or a different organic vapor contaminant concentration—see U.S. patent application Ser. No. 61/180,492, entitled Multilayer Colorimetric Sensor Arrays filed on the same day as this patent application. The window pane(s) when viewed normal thereto may take on a variety of shapes in addition to circular, for example, rectangular, elliptical, triangular, pentagonal, hexagonal, heptagonal, octagonal, etc.

During filter cartridge use, ambient air travels through a series of intake ports 43 located in the air throughput surface 32. This air then passes through the filter material 42 where contaminants present in the ambient air are removed. In passing through the filter material 42, the air first enters the filter material 42 at first major surface 45 and exits it at second major surface 47. After passing through the filter material 42, the air may enter a plenum 44 juxtaposed against the base 46 of the filter cartridge 12. Air present in the plenum 44 then passes through the filter cartridge exit port 48. The filtered air may then enter the interior gas space of the mask body 14 where it may be inhaled by the respirator wearer. As the air travels through the filter cartridge, contaminants that are present in the air interact with the ESLI. Once a sufficient concentration of contaminants has interacted with the ESLI, it will change color. The color change may be in the form of a gradient, and therefore it may be desirable to mask off the color changes that are not needed to be seen. Accordingly, the window 38 provided for this purpose must be appropriately positioned along the sidewall 26 of the housing 22. The positioning of the window 38 may depend on the particular ESLI that is being used, the active particulate, the location of the ESLI and active particulate within the filter cartridge 12, and governmental (e.g. NIOSH) requirements. The window registration position may be disposed axially in the y dimension of the cartridge between the first and second major surfaces 45, 47 of the filter material 42. In some embodiments, the registration position may be located approximately midway between the first and second major surfaces 45, 47 of the filter material 42, whereas in other embodiments the registration position may be disposed axially closer to the second major surface 47 than the first major surface 45.

Figure 5:
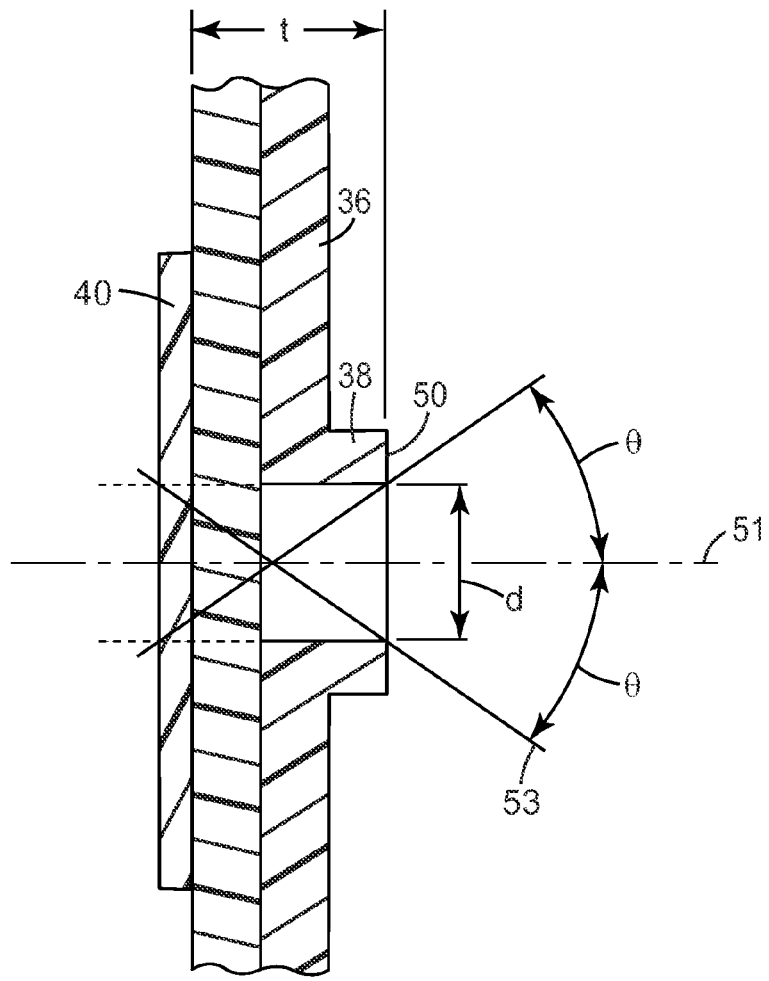
FIG. 5 is an enlarged cross-section of the housing 22 and the cover extension 36.

Some ESLIs may appear to have a different color when not viewed 90 degrees from the indicator. To preclude reader error from such non-normal viewing and to allow for sufficient visibility of the indicator, the window, as shown in FIG. 5, is preferably configured so that the ESLI only can be viewed through a cone of visibility defined by an angle omega θ that is about 20 to 70 degrees, typically about 30 to 60 degrees, and still more typically about 45 to 55 degrees. Angle θ is the angle between a line 51 that extends normal from the window to a line 53 offset laterally from that line 51 to where the ESLI can no longer be seen through the window 38. The window typically will have a diameter d of about 2 to 10 millimeters (mm), more commonly about 3 to 5 mm. The thickness t of the window may be from about 1.2 to 12 mm, more typically about 3 to 6 mm. The ratio of window thickness t to window diameter d (aspect ratio) typically is about 0.1 to 6, more typically 0.5 to 3, and still more typically about 1 to 1.5. The surface or open area of the window typically is about 3 to 1000 mm$^2$, more commonly 7 to 20 mm$^2$. The cover extension 36 preferably is integral to the cover 24 so that the masking feature can be provided at the same time that the cover 24 is manufactured. A reference indicator 52, which has a shape similar to the shape of the window pane on the opaque extension 36, may be placed on the extension 36 adjacent to the window 38 so that the wearer can identify the particular color, hue, and/or reflectivity of the ESLI, which indicates the need to change the filter cartridge.

In manufacturing a filter cartridge in connection with the present invention, the filter cartridge housing, filter media, and cover may be manufactured using presently-known or later developed techniques. The filter cartridge housing and cover may be made using a injection molding operations. A first scrim 54 may be positioned at the top of the plenum 44 before introducing the filter material 42. The filter material 42 may be a filter material that removes gaseous or vapor contaminants and that comprises active particulate that is capable of sorbing one or more undesired contaminants. The sorptive media may include a variety of active particulate such as activated carbon and alumina. U.S. Pat. No. 7,309,513 to Brey et al., U.S. Pat. No. 5,696,199 to Senkus et al., U.S. Pat. No. 5,496,785 to Abler et al., and U.S. Pat. No. 5,078,132 to Braun et al., for example, describe various types of active particulate that could be used in connection with the present invention. The active particulate may be in the form of a packed or bonded bed—see, for example, U.S. Pat. No. 5,033,465 to Braun et al., and U.S. Pat. No. 6,391,429 to Senkus. The ESLI 40 may be placed against the inner surface of the housing sidewall 26 before active particulate introduction. The ESLI needs to be properly positioned relative to the y dimension so that the appropriate color change is seen through the window 38 when the filter service life has ended. Small deviations in positioning along the y axis can result in large differences in the response signal. A second scrim 56 may be placed on the upstream surface 45 of the filter material 42. The upstream scrim 56 may comprise a suitable fibrous medium that helps retain the active particulate in place and provides a low pressure drop thereacross and helps adequately distribute the air that passes through it. Examples of materials that may be used for scrims 54 and 56 include nonwoven polyesters and nonwoven polypropylenes such as spunbond webs. After the filter material 42 and scrims 54 and 56 have been properly positioned in the cartridge housing 22, the cartridge cover 24 may be secured to the housing sidewall 26. The securement may be achieved at flange 34, for example, by mechanical, chemical, or physical means including welding or adhesive bonding, or any other suitable means. When the cover 24 is positioned on the housing 22 such that the filter cartridge 12 is properly assembled, the window 38 will be in its proper registration position. The invention thus allows such registration to be achieved using manufacturing techniques that are commonplace in the industry and that enable consistent reproducible positioning of the window.

ESLIs that may be used in connection with the present invention preferably are passive sensors that absorb or adsorb gas vapors that are desired to be filtered from the air. The ESLI may be essentially any known or later developed device (passive or active) that is capable of providing the proper indication to the respirator wearer that the filter has met the end of its useful life. Examples of passive end-of-service-life-indicators have been described in U.S. Patent Publications 2000/0063575A1 and 2008/0063874A1 to Rakow et al. ESLIs that may be employed include those that respond to organic vapors, reactive gases such as acidic (for example, $SO_2$, $Cl_2$, HCl, HCN, HF, $H_2S$ and oxides of nitrogen) and basic gases (for example, ammonia, methylamine), and cynogen chloride and formaldehyde.

Figure 6:
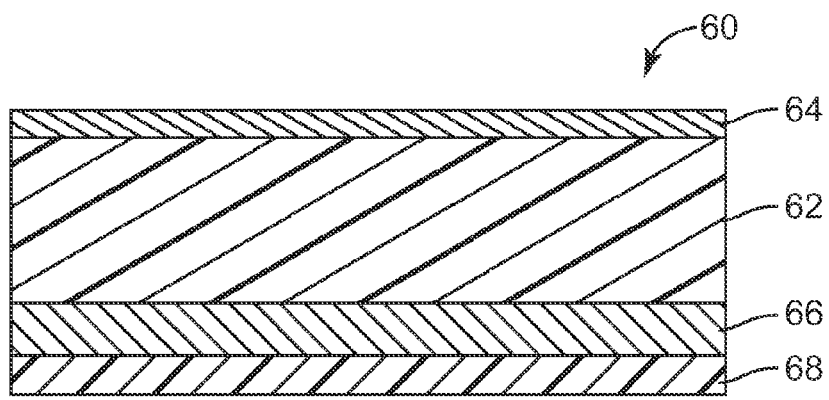
FIG. 6 is a cross-section of an ESLI 60.

As shown in FIG. 6, these end-of-service-life-indicators 60 may comprise a thin film multi-layer construction that can sorb a vapor of interest flowing from the gas inlet to the gas outlet of the respirator filter cartridge. Such passive ESLIs typically contain a porous detection layer 62, a semi-reflective layer 64, and a reflective layer 66. The porous detection layer 62 has a thickness that will change in the presence of a particular vapor. The semi-reflective layer 64 is viewable from the outside of the ESLI and is generally not permeated by the vapor. The reflective layer 66 is generally permeable to the vapor and is in sufficient proximity to the filter media such that the vapor can pass through the reflective layer into the detection layer 62 and change the detection layer optical thickness sufficiently to cause a visibly discernible change in the indicator appearance as viewed through the semi-reflective layer 64.

An ESLI that is used in connection with the present invention may be rigid or flexible. It can be secured to the housing cartridge interior by various means such as adhesive, physical, packing techniques, or mechanical engagement. Flexible indicators desirably are sufficiently bendable without fracturing so that they can be made using one or more roll processing steps.

The ESLI may include an optional substrate 68 such as glass or a flexible plastic film that may be handled in one or more roll processing steps. The substrate desirably has sufficiently low vapor permeability so that the vapor(s) of interest will not be transmitted into or out of the ESLI detection layer. A porous substrate may be placed between the reflective layer and the sorbent media. For example, vapors of interest could be allowed to pass from the sorbent media through the permeable substrate and reflective layer and thence into the detection layer. The overall thickness of the ESLI (excluding a substrate) may be about 0.5 to 2 micrometers (μm).

The semi-reflective and reflective layers each may be made from a variety of materials that provide diffuse or preferably specular light reflection and that can cooperate when appropriately spaced apart to provide a readily visibly perceptible indicator appearance change. Suitable semireflective and reflective layer materials include metals such as aluminum, chromium, gold, nickel, silicon, silver, palladium, platinum, titanium and alloys containing such metals; metal oxides such as chrome oxide, titanium oxide and aluminum oxide; and the multilayer optical films (including birefringent multilayer optical films) described in U.S. Pat. No. 5,699,188 (Gilbert et al.), U.S. Pat. No. 5,882,774 (Jonza et al.) and U.S. Pat. No. 6,049,419 (Wheatley et al.), and PCT Published Application No. WO 97/01778 (Ouderkirk et al.). The semireflective and reflective layers may be the same or different. Metal nanoparticle coatings (e.g., metal nanoparticle inks) may be employed to form the reflective layer, as described in U.S. patent application Ser. No. 11/530,619 entitled Permeable Nanoparticle Reflector.

The semireflective layer is less reflective than the reflective layer and transmits some incident light. The semireflective layer may, for example, have a physical thickness of about 2 to about 50 nanometers (nm), light transmission at 500 nm of about 20 to about 80%, and reflectance at 500 nm of about 80 to about 20%. The semireflective layer may itself be impermeable to vapor (and if so desirably is continuous) and optionally coated on or otherwise adjacent to a suitable substrate. The semireflective layer also may be permeable to vapor (and if so may, for example, be discontinuous or semi-continuous) and coated on or otherwise adjacent to a suitably vapor-impermeable substrate. The face of the semireflective layer adjacent the detection layer desirably is flat to within about ±10 nm.

The reflective layer may, for example, have a physical thickness of about 1 to about 500 nm, light transmission at 500 nm of about 0 to about 80%, and reflectance at 500 nm of about 100 to about 20%. The reflective layer preferably is porous, patterned, discontinuous, semicontinuous or otherwise sufficiently permeable so that vapor can pass from the sorbent media through the reflective layer into the detection layer.

The detection layer mixture may be homogeneous or heterogeneous, and may, for example, be made from a mixture of inorganic components, a mixture of organic components, or a mixture of inorganic and organic components. Detection layers made from a mixture of components may provide improved detection of groups of analytes. The detection layer desirably has a range of pore sizes or a surface area selected to provide vapor sorption characteristics like those of the sorbent media. Suitable porosity can be obtained using porous materials such as foams made from high internal phase emulsions, such as those described in U.S. Pat. No. 6,573,305 B1 (Thunhorst et al.). Porosity may also be obtained via carbon dioxide foaming to create a microporous material (see "Macromolecules", 2001, vol. 34, pp. 8792-8801), or by nanophase separation of polymer blends (see "Science", 1999, vol. 283, p. 520). In general, the pore diameters preferably are smaller than the peak wavelength of the desired indicator coloration. Nano-sized pores are preferred, e.g., with average pore sizes of about 0.5 to about 20 nm, 0.5 to about 10 nm, or 0.5 to about 5 nm.

Representative inorganic detection layer materials include porous silica, metal oxides, metal nitrides, metal oxynitrides and other inorganic materials that can be formed into transparent and porous layers of appropriate thickness for producing color or a colorimetric change by optical interference. For example, the inorganic detection layer materials may be silicon oxides, silicon nitrides, silicon oxynitrides, aluminum oxides, titanium oxides, titanium nitride, titanium oxynitride, tin oxides, zirconium oxides, zeolites or combinations thereof. Porous silica is an especially desirable inorganic detection layer material due to its robustness and compatibility with wet etching treatments.

Representative porous silica materials are described in Ogawa et al., *Chem. Commun.* pp. 1149-1150 (1996), in Kresge et al., *Nature*, Vol. 359, pp. 710-712 (1992), in Jia et al., *Chemistry Letters*, Vol. 33(2), pp. 202-203 (2004) and in U.S. Pat. No. 5,858,457 (Brinker et al.). A variety of organic molecules may also be employed as organic templates. For example, sugars such as glucose and mannose may be used as organic templates to generate porous silicates, see Wei et al, *Adv. Mater.* 1998, Vol. 10, p. 313 (1998).

Representative organic detection layer materials include polymers, copolymers (including block copolymers) and mixtures thereof prepared or preparable from classes of monomers including hydrophobic acrylates and methacrylates, difunctional monomers, vinyl monomers, hydrocarbon monomers (olefins), silane monomers, fluorinated monomers, hydroxylated monomers, acrylamides, anhydrides, aldehyde-functionalized monomers, amine- or amine salt-functionalized monomers, acid-functionalized monomers, epoxide-functionalized monomers and mixtures or combinations thereof U.S. Patent Application Publication No. US 2004/0184948 A1 contains an extensive list of such monomers. The above-mentioned polymers having intrinsic microporosity (PIMs) provide particularly desirable detection layers. PIMs typically are non-network polymers that form microporous solids. Due to their typically highly rigid and contorted molecular structures, PIMs are unable to fill space efficiently, thus providing the disclosed microporous structure. Suitable PIMs include, but are not limited to, polymers disclosed in "Polymers of intrinsic microporosity (PIMs): robust, solution-processable, organic microporous materials," Budd et al., *Chem. Commun.*, 2004, pp. 230-231. Additional PIMs are disclosed in Budd et al., *J. Mater. Chem.*, 2005, 15, pp. 1977-1986, in McKeown et al., *Chem. Eur. J.* 2005, 11, No. 9, 2610-2620 and in Published PCT application No. WO 2005/012397 A2 (McKeown et al.).

The thickness of the detection layer may also be patterned, for example, as described in U.S. Pat. No. 6,010,751 (Shaw et al.). The pattern may disappear (for example when a thinner portion swells to the same thickness as a thicker portion) or appear (for example, when a portion shrinks to a lesser thickness than an adjacent portion). When providing a reference indicator that would allow the wearer to easily identify when the trip point has been reached, the detection layer thickness can be altered to achieve an appearance that is identical to the tripping point of the ESLI. Alternatively, an ESLI reference that is structurally identical to the ESLI that would be seen through the window of the present invention can be forced to its response signal and preserved in that condition. Or the detection layer may be made thicker so that the reference ESLI displays the desired response signal. This preserved ESLI may be placed on the exterior of the filter cartridge as a reference indicator so that a comparison can be made between it and the image seen through the window. When the ESLI that is seen through the window appears to be the same as the reference indicator, the wearer knows that the filter cartridge has met the end of its service life. It is also possible to print a reference color that matches or approximates the end state of the sensor using an appropriate dye or pigment.

The ESLI may include additional layers or elements if desired. For example, a porous layer of sorbent-loaded composite (e.g., a web of activated carbon particles ensconced in a matrix of fibrillated PTFE such as is described in the above-mentioned U.S. Pat. No. 4,208,194) may be placed between the reflective layer and the sorbent media, to homogenize vapors permeating into the indicator or otherwise moderate the indicator response to conditions in the sorbent media. When the ESLI changes to the color or hue that indicates that the filter cartridge should be replaced, the change in such appearance reflects a specified level of sorbent depletion that mandates replacement of the filter cartridge. In other words, the manufacturer of the filter cartridge may adjust the selection of the particular ESLI and the positioning of the window into its registration position such that the particular level of sorbent depletion can be achieved. The selection of the level of sorbent depletion may depend on a variety of factors, including providing a sufficient buffer so that the sorbent is not 100% depleted when the filter cartridge is identified as being needed to be replaced. The level of sorbent depletion may, for example, be identified to provide one to three hours of additional use so that the wearer has adequate time to notice that the ESLI has undergone the color change indicating satisfaction of the response signal or need for cartridge replacement.

The filter cartridge also may include one or more layers of filter media fashioned for removing particulates. Fibrous particulate filters may be used upstream or downstream to the active particulate to remove particulate contaminants from the ambient air. A variety of fibrous webs may be suitable for use as particulate filters. These webs typically are nonwoven fibrous structures that can be made from techniques such as air-laid processes, wet-laid processes, hydro-entanglement, spunbond processes, and meltblown processes such as described in Van A. Wente, *Superfine Thermoplastic Fibers*, 48 INDUS. ENGN. CHEM. 1342-46 and in Report No. 4364 of the Naval Research Laboratories, published May 25, 1954, entitled *Manufacture of Super Fine Organic Fibers* by Van A. Wente et al. The fibrous webs can be made using combinations of these techniques and combinations of such fibers. Microfibers, particularly meltblown microfibers, are particularly suitable for use in fibrous webs that are used as filters. As used in this document, "microfiber" means fiber(s) that have an effective diameter of about 35 micrometers or less. Effective fiber diameter can be calculated using equation number 12 in Davies, C. N., *The Separation of Airborne Dust and Particles*, INST. MECH. ENGN., LONDON PROC. 1B (1952). For filtering applications, the microfibers typically have an effective fiber diameter of less than about 30 micrometers, more typically, about 1 to about 15 micrometers. Fibers made from fibrillated films may also be used—see, for example, U.S. Pat. Nos. RE30,782, RE32,171, 3,998,916 and 4,178,157 to Van Turnout. Nonwoven webs that are made by the process of the present invention may exhibit quality factors QF that exceed 2, 2.1, 2.2, and 2.3.

Staple fibers also may be combined with the microfibers to improve web loft, that is, to reduce its density. Reducing web density can lower the pressure drop across the web, making it easier for air to pass through the filter. Lower pressure drops are particularly desirable in personal respiratory protection devices because they make the respirator more comfortable to wear. When the pressure drop is lower, less energy is needed to draw air through the filter. A respirator wearer who dons a negative pressure mask—that is a respirator that requires negative pressure from the wearer's lungs to draw air through the filter—does not have to work as hard to breath filtered air. Lower energy requirements also can be beneficial in powered filtering systems to reduce costs associated with powering the fan and to extend the service life of a battery in a battery powered system. In a typical nonwoven fibrous filter, no more than about 90 weight percent staple fibers are present, more typically no more than about 70 weight percent. Often, the remainder of the fibers are microfibers. Examples of webs that contain staple fibers are disclosed in U.S. Pat. No. 4,118,531 to Hauser.

Although the present invention has been illustrated using a full-face respirator mask that covers the wearer's nose, mouth, and eyes, the present invention also may be used in conjunction with half-masks that cover only the wearer's nose and mouth. Further, the filter cartridges that are used in connection with the present invention may be permanently or removably attached to the mask body. Additionally, the respirator may have one or more filter cartridges that are attachable to the mask body. The harness also may come in a variety of configurations and may include additional parts such as a crown member to support the respirator on a wearer's head. Accordingly, a variety of embodiments are contemplated by the invention when providing respirator masks that have end-of-life-service-indicators disposed on the filter cartridge.

EXAMPLE

ESLI Preparation

In a 2.0 liter (L) three-neck round bottomed flask, 33.4357 grams (g) of 3,3,3',3'-tetramethyl-1,1'-spirobisindane-5,5',6,6'-tetrol (tetrol) and 19.8016 g of tetrafluoroterephthalonitrile (TFTN) were dissolved in 900 milliliters (mL) of anhydrous N,N-dimethyl formamide (DMF). The solution was stirred with a mechanical stirrer, and nitrogen was bubbled through the solution for one hour. To this solution was added 81.4491 g of potassium carbonate. The flask was placed in an oil bath at 68° C. The mixture was stirred at this elevated temperature under a nitrogen atmosphere for 65 hours. The polymerization mixture was poured into 9.0 L of water. The precipitate formed was isolated by vacuum filtration and washed with 600 mL of MeOH. The isolated material was spread out in a pan and allowed to air dry overnight. The solid was placed in ajar and dried under vacuum at 68° C. for 4 hours. The resulting yellow powder was dissolved in 450 mL of THF. This solution was poured slowly into 9.0 L of methanol. The precipitate formed was isolated by vacuum filtration. The isolated material was spread out in a pan and allowed to air dry overnight. The solid was placed in ajar and dried under vacuum at 68° C. for 4 hours. The precipitation in methanol was performed one more time. The resulting dried, bright yellow polymer weighed 42.80 g. Analysis of the polymer by GPC using light scattering detection showed the material to have a $M_n$ of approximately 30,900.

A metalized polyethylene terephthalate (PET) substrate was prepared by evaporatively depositing a 10 nm-thick Ni metal layer onto Melinex ST505 clear PET. A 4% by weight solution of TFTN-PIM in chlorobenzene was prepared and solution deposited onto the Ni-coated PET by spin coating, to a thickness of approximately 600 nm. A silver nanoparticle layer was solution deposited onto the TFTN-PIM layer using 100 g of stock nanosilver suspension (DGP-40LT-15C from Advanced Nanoproducts, Korea, 40% by weight silver in methanol) diluted with 100 g of 1-methoxy-2-propanol. The silver suspension was spin coated onto the PIM layer. After deposition, the overall sensor construction was heated at 150 degrees C. for 1 hour to sinter the silver nanoparticles. The resulting thin-film indicator had a green appearance when visually observed normally through the clear PET substrate.

Cartridge Assembly

A filter cartridge housing was molded from clear styrene (K-Resin from Chevron-Phillips). A scrim made from Remay™ spunbond polyester (available from Fiberweb of London, United Kingdom) was welded into place in the bottom of the housing. An optical transfer adhesive (3M Optically Clear Adhesive 8172 from 3M Company) was used to adhere the indicator to the transparent inner wall of the housing by making a bond between the PET and the cartridge sidewall. The remaining filtration cartridge volume was then filled with 45.8 g of activated carbon sorbent (GG carbon from Kuraray Corp., at 12×20 mesh size).

A cartridge inlet cover having an extension as shown in FIGS. 1-3 and was made using a rapid-prototype ABS plastic. A second scrim also made from Remay™ spunbond polyester was glued to the inner surface of the cover. The cover-scrim assembly was then sonically welded to the housing, compressing the carbon in the process. The window had a thickness t of about 5 mm, a diameter d of about 4.2 mm, a surface area of about 13.9 mm², and a cone angle of visibility θ of about 50 degrees. The resulting cartridge exhibited an ESLI that appeared green in color when seen through the window before any exposure. The indicator was out of view when the cartridge was tilted such that the viewer's line of sight was outside angle θ.

This invention may take on various modifications and alterations without departing from its spirit and scope. Accordingly, this invention is not limited to the above-described but is to be controlled by the limitations set forth in the following claims and any equivalents thereof.

This invention also may be suitably practiced in the absence of any element not specifically disclosed herein.

All patents and patent applications cited above, including those in the Background section, are incorporated by reference into this document in total. To the extent there is a conflict or discrepancy between the disclosure in such incorporated document and the above specification, the above specification will control.

What is claimed is:

1. A filter cartridge that comprises:
   (a) a filter material;
   (b) an end-of-service-life-indicator (ESLI);
   (c) a cartridge housing into which the filter material and ESLI are disposed;
   (d) a window through which the ESLI may be viewed, the window being configured such that the ESLI can only be seen through the window within a cone defined by an angle θ of 20 to 70 degrees.

2. The filter cartridge of claim 1, wherein angle θ is 30 to 60 degrees.

3. The filter cartridge of claim 1, wherein angle θ is 45 to 55 degrees.

4. The filter cartridge of claim 1, wherein the window is circular and has a diameter of 2 to 10 mm.

5. The filter cartridge of claim 1, wherein the window is circular and has a diameter of 3 to 5 mm.

6. The filter cartridge of claim 1, wherein the window has a thickness t of 1.2 to 12 mm.

7. The filter cartridge of claim 1, wherein the window has a thickness t of 3 to 6 mm.

8. The filter cartridge of claim 1, wherein the window has an aspect ratio of 1 to 6.

9. The filter cartridge of claim 1, wherein the window has an aspect ratio of 0.5 to 3.

10. The filter cartridge of claim 1, wherein the window has an aspect ratio of 1 to 1.5.

11. The filter cartridge of claim 1, wherein the window has a surface area of about 3 to 100 $mm^2$.

12. The filter cartridge of claim 1, wherein the window has a surface area of about 7 to 20 $mm^2$.

13. The filter cartridge of claim 1, wherein the window has a frame located about a window pane.

14. The filter cartridge of claim 13, wherein the cartridge housing has a sidewall that is transparent in the vicinity of the window.

15. The filter cartridge of claim 14, wherein the window has first and second panes, the first pane being disposed in the housing sidewall and the second pane being disposed in an extension of a cover that is attached to the cartridge housing.

16. The filter cartridge of claim 15, wherein the pane that is disposed in the cartridge housing sidewall is fluid impermeable, and wherein the pane that is disposed in the cover extension is fluid permeable.

17. The filter cartridge of claim 1, wherein the window comprises a frame located about a window pane.

18. A mask body that is adapted to fit at least over a person's nose and mouth and that comprises one or more of the filter cartridges of claim 1, attachable thereto.

19. A respirator that comprises the mask body of claim 18.

20. A respirator that comprises a mask body; a harness attached to the mask body; and one or more filter cartridges that are attachable to the mask body, the cartridges comprising a housing into which a filter material and an ESLI are disposed, the housing having a sidewall onto which the ESLI is juxtaposed against, a cover through which air may pass before being filtered by the filter material, and a window being positioned in the vicinity of the ESLI so that the ESLI can be seen therethrough, the window being adapted to provide a viewer with a cone of visibility that is defined by an angle of 20 to 70 degrees, the window further having an aspect ratio of 0.5 to 3, a thickness of 1.2 to 12 mm, and a surface area of 7 to 20 $mm^2$.

* * * * *

UNITED STATES PATENT AND TRADEMARK OFFICE
CERTIFICATE OF CORRECTION

| | | |
|---|---|---|
| PATENT NO. | : 8,365,723 B2 | Page 1 of 1 |
| APPLICATION NO. | : 12/470920 | |
| DATED | : February 5, 2013 | |
| INVENTOR(S) | : Richard J. Poirier | |

It is certified that error appears in the above-identified patent and that said Letters Patent is hereby corrected as shown below:

In the Specifications:

<u>Column 7</u>

Line 42, delete "thereof" and insert -- thereof. --, therefor.

<u>Column 9</u>

Line 57, delete "ajar"" and insert -- a jar --, therefor.

<u>Column 9</u>

Line 62, delete "ajar" and insert -- a jar --, therefor.

Signed and Sealed this
Eleventh Day of June, 2013

Teresa Stanek Rea
*Acting Director of the United States Patent and Trademark Office*